US008828091B2

(12) United States Patent
Deal

(10) Patent No.: US 8,828,091 B2
(45) Date of Patent: Sep. 9, 2014

(54) MOVABLE STENT REINFORCEMENT

(75) Inventor: Travis Deal, Freedom, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1883 days.

(21) Appl. No.: 11/386,663

(22) Filed: Mar. 23, 2006

(65) Prior Publication Data
US 2007/0225679 A1 Sep. 27, 2007

(51) Int. Cl.
A61F 2/04 (2013.01)
A61M 27/00 (2006.01)

(52) U.S. Cl.
CPC .............. A61M 27/008 (2013.01); A61F 2/04 (2013.01); A61F 2002/048 (2013.01); A61M 27/002 (2013.01)
USPC ...................................... 623/23.66

(58) Field of Classification Search
CPC ............. A61F 2/04; A61F 2002/048; A61F 2002/047; A61M 27/00; A61M 27/002; A61M 27/008
USPC ................. 623/23.7, 23.65, 23.64, 1.16, 623/23.66–23.69; 604/8–9
See application file for complete search history.

(56) References Cited

U.S. PATENT DOCUMENTS

| 4,850,999 | A | * | 7/1989 | Planck | 623/1.44 |
| 4,874,360 | A | | 10/1989 | Goldberg et al. | |
| 5,084,065 | A | * | 1/1992 | Weldon et al. | 623/1.44 |
| 5,123,917 | A | * | 6/1992 | Lee | 623/22.26 |
| 5,176,625 | A | | 1/1993 | Brisson | |
| 5,246,445 | A | | 9/1993 | Yachia et al. | |
| 5,681,274 | A | | 10/1997 | Perkins et al. | |
| 5,871,537 | A | * | 2/1999 | Holman et al. | 623/1.23 |
| 5,971,967 | A | * | 10/1999 | Willard | 604/264 |
| 6,053,943 | A | * | 4/2000 | Edwin et al. | 623/1.25 |
| 6,124,523 | A | * | 9/2000 | Banas et al. | 623/1.15 |
| 6,214,037 | B1 | | 4/2001 | Mitchell et al. | |
| 6,379,382 | B1 | * | 4/2002 | Yang | 623/1.42 |
| 6,656,146 | B1 | * | 12/2003 | Clayman et al. | 604/8 |
| 6,685,744 | B2 | | 2/2004 | Gellman et al. | |

(Continued)

FOREIGN PATENT DOCUMENTS

DE 20 2005 001 416 U1 5/2005
EP 1 685 813 A1 8/2006

(Continued)

OTHER PUBLICATIONS

Yamaguchi, O. et al., "Prototype of a Reflux-Preventing Ureteral Stent and its Clinical Use," [Abstract], Urology, Oct. 1992, pp. 326-329, vol. 40, No. 4. [Retrieved online from Entrez PubMed on Aug. 29, 2005, URL: <http://www.ncbi.nlm.nih.gov>.].

(Continued)

Primary Examiner — Andrew Iwamaye

(57) ABSTRACT

The invention is directed towards a medical device including an elongate member having a side wall defining a lumen configured to convey a fluid within a body of a patient. The medical device includes a reinforcement member configured to be selectively coupled to the side wall of the elongate member at a first axial location and a second axial location, the second axial location being axially offset from the first axial location. In some embodiments, the reinforcement member includes a side wall defining a lumen and the elongate member is configured to extend through the lumen defined by the side wall of the reinforcement member.

18 Claims, 16 Drawing Sheets

(56) References Cited

U.S. PATENT DOCUMENTS

| | | |
|---|---|---|
| 6,764,519 B2 | 7/2004 | Whitmore, III |
| 6,849,069 B1 | 2/2005 | Clayman et al. |
| 6,887,215 B2 | 5/2005 | McWeeney |
| 6,953,476 B1* | 10/2005 | Shalev .................. 623/1.15 |
| 2001/0020181 A1* | 9/2001 | Layne .................. 623/1.13 |
| 2001/0021835 A1* | 9/2001 | Mitchell et al. .......... 604/385.17 |
| 2002/0026231 A1* | 2/2002 | Shannon et al. ........... 623/1.13 |
| 2002/0151957 A1* | 10/2002 | Kerr .................. 623/1.13 |
| 2003/0036792 A1* | 2/2003 | Richter et al. ............ 623/1.12 |
| 2003/0199993 A1* | 10/2003 | Gellman et al. .......... 623/23.75 |
| 2004/0059279 A1 | 3/2004 | McWeeney et al. |
| 2004/0111828 A1* | 6/2004 | Evans .................. 15/414 |
| 2004/0193092 A1* | 9/2004 | Deal .................. 604/8 |
| 2005/0075622 A1* | 4/2005 | Levine et al. .................. 604/500 |
| 2005/0240278 A1* | 10/2005 | Aliski et al. .................. 623/23.7 |
| 2006/0253104 A1* | 11/2006 | Pandey et al. .................. 604/540 |

FOREIGN PATENT DOCUMENTS

| | | | |
|---|---|---|---|
| WO | WO 96/30070 A1 | 10/1996 | |
| WO | WO 99/09911 A1 | 3/1999 | |
| WO | WO 9909911 A2 * | 3/1999 | ............... A61F 2/01 |

OTHER PUBLICATIONS

International Search Report and Written Opinion of the International Searching Authority for PCT/US2007/063057 mailed on Oct. 5, 2007, 12 pages.

* cited by examiner

MOVABLE STENT REINFORCEMENT

BACKGROUND

The disclosed invention relates generally to a medical device and more particularly to a ureteral stent.

Ureteral stents are typically placed within a urinary tract of a patient such that one end portion of the ureteral stent is located in a kidney of the patient and the other end portion of the ureteral stent is located in either a bladder or a ureter of the patient. Some known ureteral stents include retention members configured to retain the ureteral stent in a desired position within the patient. Known ureteral stents are typically positioned within the urinary tract of the patient by placing a guidewire within the patient, sliding the ureteral stent on the guidewire, and then pushing the ureteral stent along the guidewire into a desired position using a push rod.

Known ureteral stents are designed to provide optimal functionality while minimizing patient discomfort. Some design features that provide improved comfort, however, may decrease functionality. For example, hard stents are known to be more resistant to deformation and easier to position within the urinary tract than soft stents. As the hardness of the stent increases, however, the patient will generally experience greater discomfort while the stent is within the urinary tract. Conversely, softer stents may alleviate patient discomfort, but they are generally more difficult to insert and more susceptible to deformation or kinking once inserted into the patient.

To accommodate the need for both comfort and functionality, some known ureteral stents are configured such the stent hardness or durometer varies spatially along the longitudinal axis of the stent. In this manner, one section of the stent can be relatively hard, while another section can be relatively soft. Because the location of the hard and soft portions of known dual durometer stents is fixed, such stents do not accommodate circumstances in which the unique conditions of a patient require the hard portion to be in a location different from that supplied in the basic stent design. Such design flexibility may be needed, for example, when the stent is subject to kinking or deformation due to a localized stricture in the ureter of a particular patient.

Thus, a need exists for a ureteral stent having a spatial variation in the strength or resistance to deformation, in which the region of increased strength can be selectively determined based on the needs of a particular patient.

SUMMARY

The invention is directed towards a medical device including an elongate member having a side wall defining a lumen configured to convey a fluid within a body of a patient. The medical device also includes a reinforcement member configured to be selectively coupled to the side wall of the elongate member at a selected one of two or more axial locations. In some embodiments, the reinforcement member includes a side wall defining a lumen and the elongate member is configured to extend through the lumen defined by the side wall of the reinforcement member.

In another embodiment, a method of selectively reinforcing a portion of a ureteral stent includes selecting a portion of the stent to be reinforced such that the portion will be disposed proximate to a stricture when the ureteral stent is inserted into a body of a patient and coupling a reinforcement member to the selected portion of the stent.

DETAILED DESCRIPTION

Figure 1A:
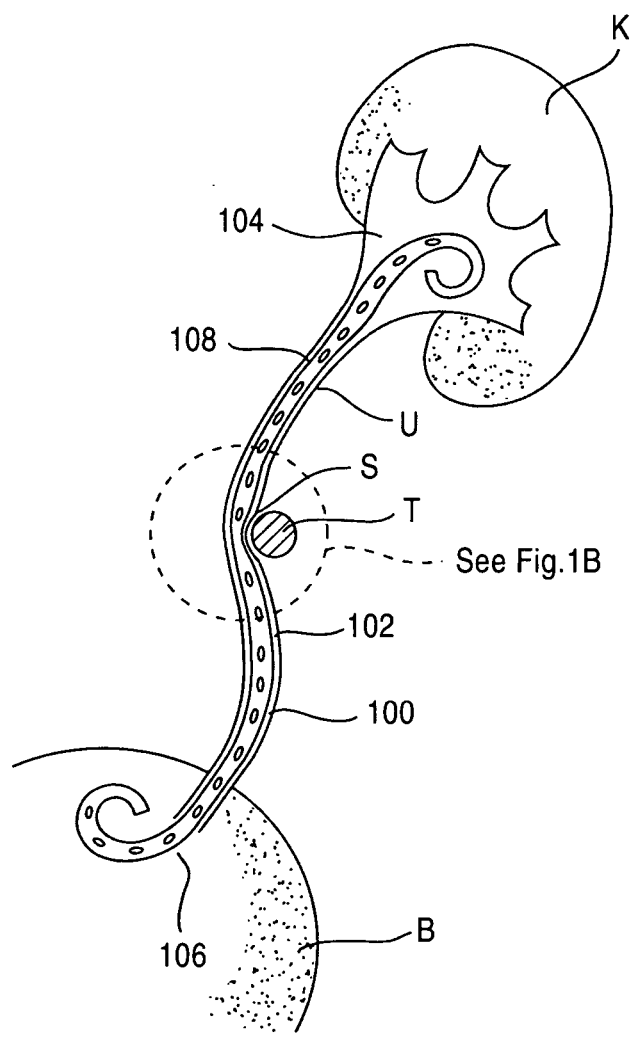
FIG. 1A illustrates a known ureteral stent disposed within the urinary tract of a patient.
Figure 1B:
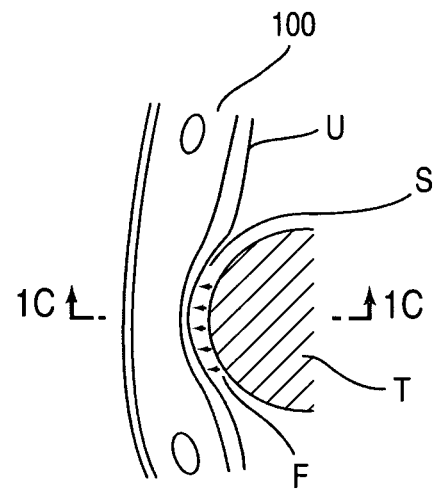
FIG. 1B is an enlarged view of a portion of the known ureteral stent as defined by region 1B in FIG. 1A.
Figure 1C:
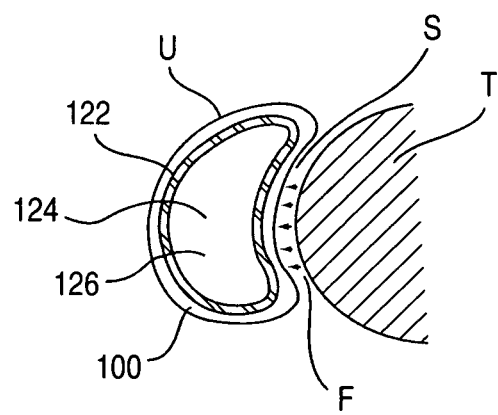
FIG. 1C is a cross-sectional view of the known ureteral stent of FIG. 1B taken along line 1C-1C in FIG. 1B.

FIGS. 1A through 1C show a known ureteral stent 100 positioned within a urinary tract of a patient. The known ureteral stent 100 is positioned within a patient such that it extends from a kidney K, through the ureter U, and to the bladder B. The known ureteral stent 100 includes an elongate member 102 having a distal end portion 104, a proximal end portion 106 and a medial portion 108 extending between the distal end portion 104 and the proximal end portion 106. The known ureteral stent 100 also includes a side wall 122 that defines a lumen 124 that can extend from the distal end portion 104 to the proximal end portion 106 of the known ureteral stent 100 to convey urine from the kidney K to the bladder B. As illustrated, the ureter U is affected by a stricture S causing a localized narrowing of the urinary tract. The stricture S may be caused by a tumor T or other physical condition within the patient. As shown in FIG. 1B, which is an enlarged view of a portion of the known ureteral stent 100 affected by the stricture S, the presence of the tumor T may increase the external force F applied to the known ureteral stent 100, causing the side wall 122 of the known ureteral stent 100 to deform. Such deformation can reduce the cross-sectional area 126 defined by the lumen 124, as shown in FIG. 1C. As the cross-sectional area 126 is reduced, the flow of urine can become restricted, thereby diminishing the effectiveness of the known ureteral stent 100. If a stricture S is known to exist in a patient, a known ureteral stent 100 may incorporate a harder side wall 122 to minimize the deformation caused by the stricture S. This solution, however, may have the undesirable effect of increasing patient discomfort.

The disclosed invention is directed towards a medical device including an elongate member having a side wall defining a lumen configured to convey a fluid within a body of a patient. The medical device includes a reinforcement member configured to be selectively coupled to the side wall of the elongate member at a first axial location and a second axial location, the second axial location being axially offset from the first axial location. In some embodiments, the reinforcement member includes a side wall defining a lumen sized such that the elongate member is disposable within the lumen defined by the side wall of the reinforcement member.

In some embodiments, the reinforcement member is configured to increase the strength or resistance to deformation of the side wall of the medical device.

In some embodiments, the device is configured such that the cross-sectional area of the lumen defined by the side wall of the elongate member at an axial location where the reinforcement member is present is at least as large as the cross-sectional area of the lumen defined by the side wall of the elongate member at an axial location devoid of the reinforcement member.

In some embodiments, a method of selectively reinforcing a portion of a ureteral stent includes selecting a portion of the stent to be reinforced such that the portion will be disposed proximate to a stricture when the ureteral stent is inserted into a body of a patient and coupling a reinforcement member to the selected portion of the stent.

Figure 2:
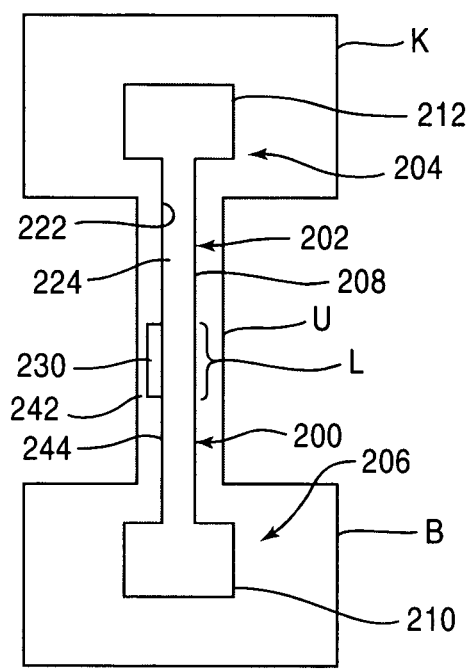
FIG. 2 is a schematic illustration of a ureteral stent according to an embodiment of the invention.

FIG. 2 is a schematic illustration of a ureteral stent 200 according to the invention that is disposed within a urinary tract of a patient. The ureteral stent 200 is positioned within a patient such that it extends from the kidney K, through the ureter U, and to the bladder B. The ureteral stent 200 is configured to facilitate the movement of fluid within a urinary tract of a patient, for example, from the kidney K to the bladder B via the ureter U.

The ureteral stent 200 includes an elongate member 202 having a distal end portion 204, a proximal end portion 206, and a medial portion 208 extending between the distal end portion 204 and the proximal end portion 206. The proximal end portion 206 includes a retention portion 210. Similarly, the distal end portion 204 includes a retention portion 212.

The retention portion 210 of the proximal end portion 206 of the ureteral stent 200 is configured to be placed within the bladder B to help prevent migration of the ureteral stent 200 upwardly toward the kidney K. Similarly, the retention portion 212 of the distal end portion 204 is configured to be placed within the kidney K to help prevent migration of the ureteral stent 200 downwardly toward the bladder B. Accordingly, the retention portions 210 and 212 are configured to help retain the ureteral stent 200 in place within the urinary tract of the patient. The retention portions 210 and 212 may be configured in a variety of different shapes and sizes, such as a loop or a "J" hook. Although the ureteral stent 200 is illustrated and described as including retention portions 210 and 212, in some embodiments, one or both of the proximal end portion 206 and the distal end portion 204 do not include retention portions.

The ureteral stent 200 includes a side wall 222 that defines a lumen 224. The lumen 224 extends from the distal end portion 204 to the proximal end portion 206 of the ureteral stent 200. In some embodiments, the lumen only extends through a portion of the ureteral stent. In other embodiments, the ureteral stent does not include a side wall that defines a lumen.

As shown in FIG. 2, the ureteral stent 200 includes a reinforcement member 230 that can be coupled to the elongate member 202 at a first axial location 242 and a second axial location 244 that is offset from the first axial location 242. In the illustrated embodiment, the axial locations 242 and 244 are located along the longitudinal axis of the elongate member 202. Although FIG. 2 shows the reinforcement member 230 being coupleable in either one of two axial locations, 242 and 244, in some embodiments, the reinforcement member 230 can be coupled to the elongate member 202 at any number of axial locations. For example, in some embodiments, the reinforcement member 230 can be positioned at any axial location along the medial portion 208 of the elongate member 202. In yet other embodiments, the reinforcement member 230 can be positioned at the distal end 204 to facilitate or ease the insertion process.

In this manner, the reinforcement member 230 can be optimally positioned based on the physical characteristics of the patient. For example, a practitioner may use conventional imaging techniques to determine the optimal position of the reinforcement member 230, e.g. adjacent to a stricture, based on the particular physical characteristics of the patient. The practitioner can couple the reinforcement member 230 to the elongate member 202 at a desired location prior to inserting the ureteral stent 200 into the patient. Allowing the practitioner to couple the reinforcement member 230 in one of several locations along the elongate member 202 eliminates the need to stock a variety of different reinforced stent designs.

The length L of the reinforcement member 230 can vary depending on the physical characteristics of the patient. For example, in cases where the stricture is large, a long reinforcement member 230 may be required to ensure that the flow of urine remains unimpeded. Conversely, if the stricture is small, the length L of the reinforcement member 230 can be relatively short.

The reinforcement member 230 can be coupled to the elongate member 202 in a number of different ways, such as by a mechanical fastener, an adhesive, or any other suitable mechanisms. Various attachment mechanisms will be discussed in more detail below.

The terms "strength" or "resistance to deformation" as used herein may be used to denote any of a number of different properties associated with a ureteral stent or a reinforcement member. For example, the terms may be used to refer to properties of the material from which the ureteral stent or reinforcement member are made, such as the yield strength, the modulus of elasticity, the modulus of rigidity, or the elongation percentage. Similarly, the terms may be used to refer to the hardness of the ureteral stent or the reinforcement member. Hardness may be characterized as the "durometer" of the material, in reference to the apparatus used to measure the hardness of the material. The terms may also be used to denote geometric characteristics of the ureteral stent or reinforcement member, such as the absence of stress concentration risers or the moment of inertia. Finally, the terms "strength" or "resistance to deformation" may be used to characterize any combination of the above properties.

The strength or resistance to deformation of the ureteral stent 200 can be increased in any number of ways. The strength can be increased by increasing the thickness of the reinforcement member 230, by eliminating stress concentration risers in the design of the ureteral stent 200, or by changing other aspects of the geometry of the ureteral stent 200 or the reinforcement member 230. The strength can also be increased by changing the material properties of the ureteral stent 200 and/or the reinforcement member 230. For example, the reinforcement member 230 can be made from a number of different materials, each having a different level of hardness. In this manner, the selection of the reinforcement member 230 can be tailored to the specific needs of each patient. For example, in regions where a high external force is expected, a reinforcement member 230 having a high hardness may be preferred. Finally, the strength may be increased by combining material properties with geometric changes. For example, the hoop strength of the ureteral stent 200 may be increased by using a reinforcement member 230 that both increases the overall wall thickness and increases the composite yield strength of the ureteral stent 200.

Figure 3A:
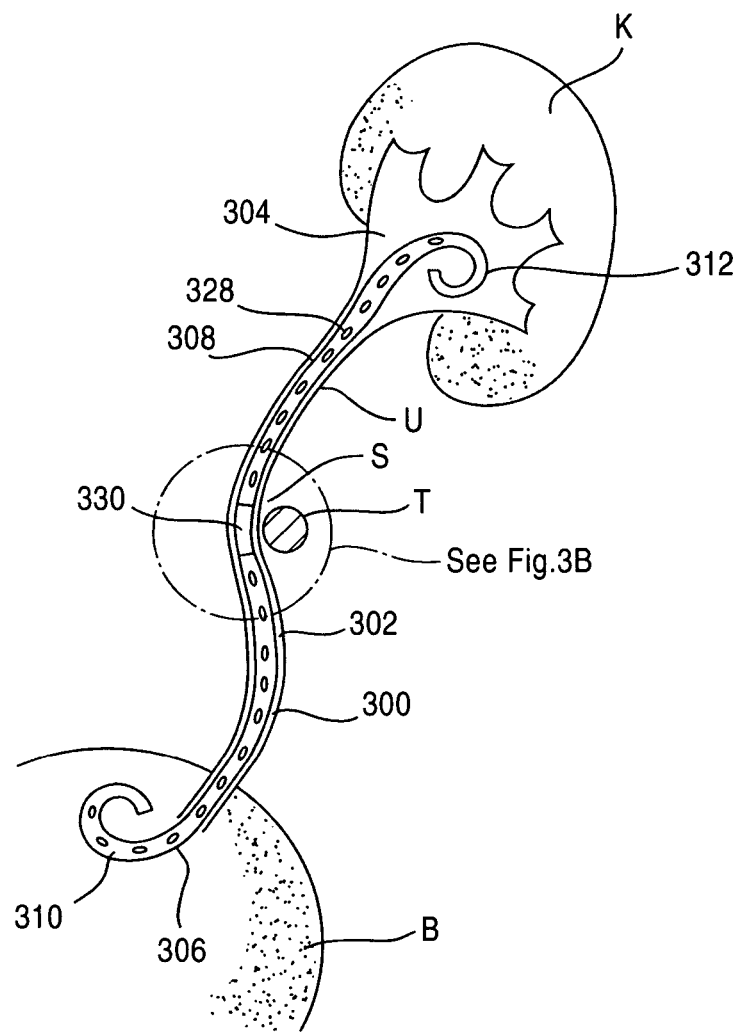
FIG. 3A illustrates a ureteral stent according to an embodiment of the invention disposed within the urinary tract of a patient.
Figure 3B:
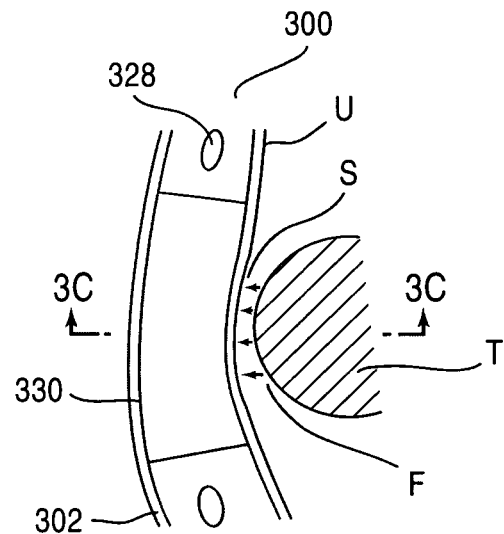
FIG. 3B is an enlarged view of a portion of the ureteral stent shown in FIG. 3A as defined by region 3B in FIG. 3A.
Figure 3C:
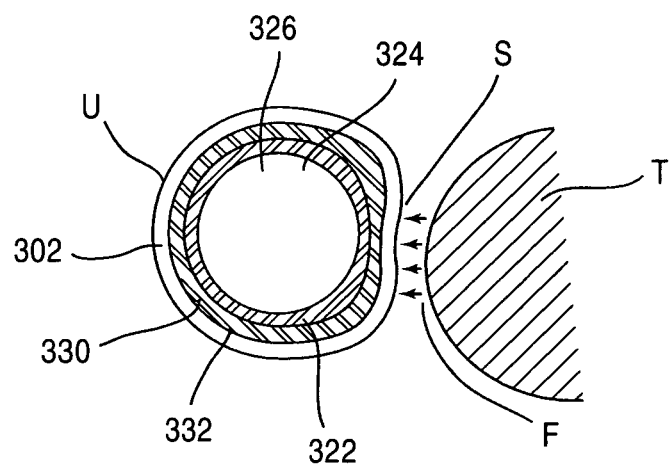
FIG. 3C is a cross-sectional view of the ureteral stent of FIG. 3B taken along line 3C-3C in FIG. 3B.

FIGS. 3A through 3C show a ureteral stent 300 according to an embodiment of the invention that is positioned within a urinary tract of a patient. The ureteral stent 300 is positioned within a patient such that it extends from a kidney K, through a ureter U, and to a bladder B. The ureteral stent 300 includes an elongate member 302 having a distal end portion 304, a proximal end portion 306 and a medial portion 308 extending between the distal end portion 304 and the proximal end portion 306. The proximal end portion 306 includes a retention portion 310. Similarly, the distal end portion 304 includes a retention portion 312. The ureteral stent 300 also includes a side wall 322 that defines a lumen 324 that can extend from the distal end portion 304 to the proximal end portion 306 of the ureteral stent 300. In the illustrated embodiment, the ureteral stent 300 includes one or more side ports 328 that allow fluid to pass from the lumen 324 to a location outside of the ureteral stent 300.

As illustrated, the ureter U is affected by a stricture S causing a localized narrowing of the urinary tract. The stricture S may be caused by a tumor T or other physical condition within the patient. As shown in FIG. 3B, which is an enlarged view of a portion of the ureteral stent 300 affected by the stricture S, the ureteral stent 300 includes a reinforcement member 330 that is coupled to the elongate member 302 at a location adjacent to the stricture S. Although the tumor T (or other physical condition) may increase the external force F applied to the ureteral stent 300, the increased strength or resistance to deformation provided by the reinforcement member 330 is sufficient to reduce the deformation of the ureteral stent 300. As a result, the cross-sectional area 326 defined by the lumen 324 in the region adjacent to the stricture S remains acceptably large or substantially unchanged, as shown in FIG. 3C.

Figure 4A:
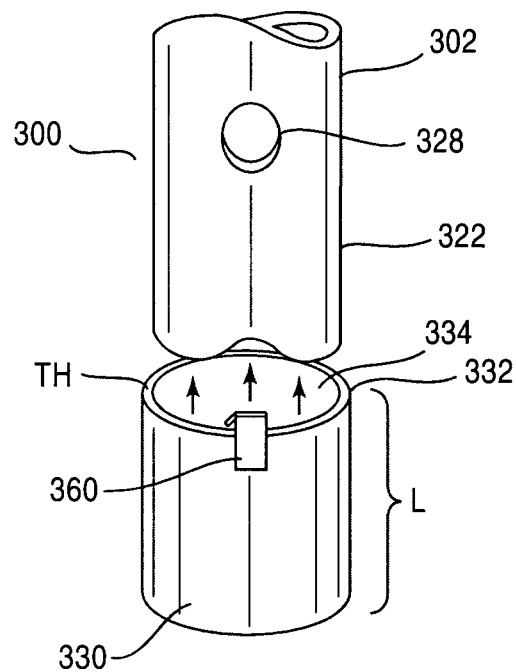
FIGS. 4A and 4B are perspective views of a ureteral stent according to an embodiment of the invention.
Figure 4B:
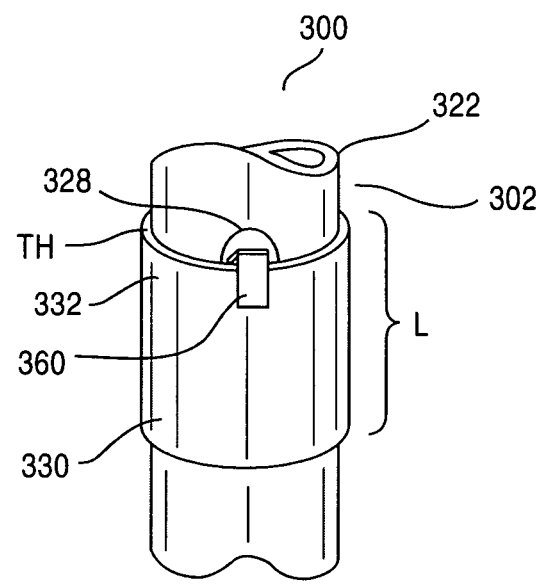

FIGS. 4A and 4B show perspective views of a portion of the ureteral stent 300 and the reinforcement member 330. The reinforcement member 330 includes a side wall 332 that defines a lumen 334 according to an embodiment of the invention. As illustrated, the lumen 334 is sized so that the elongate member 302 extends through the lumen 334, thereby positioning the reinforcement member 330 proximate to the outer surface of the side wall 322 of the elongate member 302. The reinforcement member 330 is configured so that its side wall 332 is concentric with the side wall 322 of the elongate member 302. Alternatively, the reinforcement member 330 can be configured so that its side wall 332 is eccentric with the side wall 322 of the elongate member 302. For example, an eccentric design may be desired if the thickness TH of the side wall 332 of the reinforcement member 330 varies circumferentially, as will be discussed in more detail below.

Although the reinforcement member 330 is shown and described as being positioned proximate to the outer surface of the side wall 322 of the elongate member 302, in some embodiments, the reinforcement member can be sized such that it is disposable within the lumen of the elongate member.

In the illustrated embodiment, the reinforcement member 330 is coupled to the elongate member 302 by an attachment member 360 that fits within a side port 328 of the elongate member 302. These and other attachment mechanisms will be discussed in more detail below.

Figure 5A:
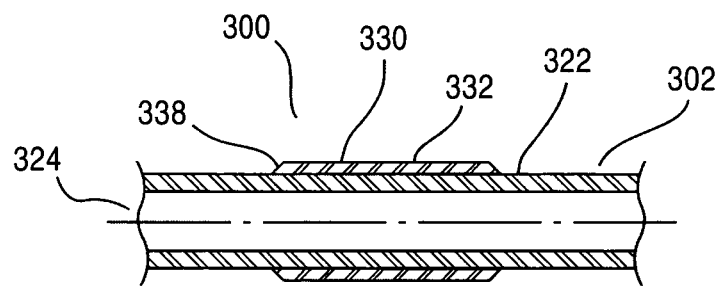
FIG. 5A is a cross-sectional view of a portion the ureteral stent of FIG. 3A showing the region where the reinforcement member is coupled.
Figure 5B:
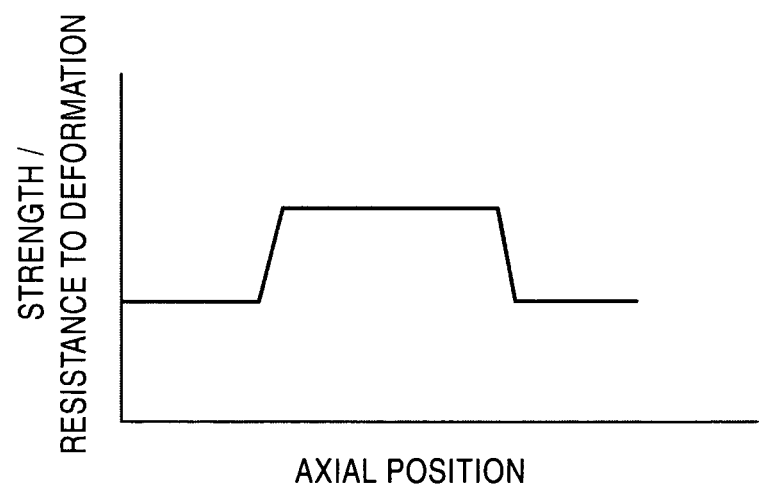
FIG. 5B is plot showing the strength of a portion of the ureteral stent of FIG. 3A as a function of axial position.

FIG. 5A illustrates a cross-sectional view of a portion of the elongate member 302 in the region where the reinforcement member 330 is coupled. FIG. 5B is a plot of the strength of the ureteral stent 300 as a function of the axial position along the portion of the elongate member 302 illustrated in FIG. 5A. As described above, strength or resistance to deformation may be characterized by any number of different properties. FIG. 5B illustrates that the strength of the ureteral stent 300 is greater in the region where the reinforcement member 330 is positioned than in the adjacent regions of the ureteral stent 300. Although the plot in FIG. 5B illustrates a stepwise increase in strength, the increase may be more gradual depending on the design of the reinforcement member 330. Furthermore, in the illustrated embodiment, the reinforcement member 330 has tapered edges 338, which allow the strength in the region of the reinforcement member 330 to vary along the length of the reinforcement member 330. The tapered edges 338 can be included to reduce patient discomfort during stent insertion. In other embodiments, the strength in the region of the reinforcement member can be constant along the length of the reinforcement member. Similarly, the reinforcement member 330 can be designed such that the strength is a non-linear function of the axial position. The reinforcement member 330 can also be designed such that the strength varies circumferentially. In this manner, the design of the reinforcement member 330 can be optimized to meet a variety of needs that may arise.

Figure 6:
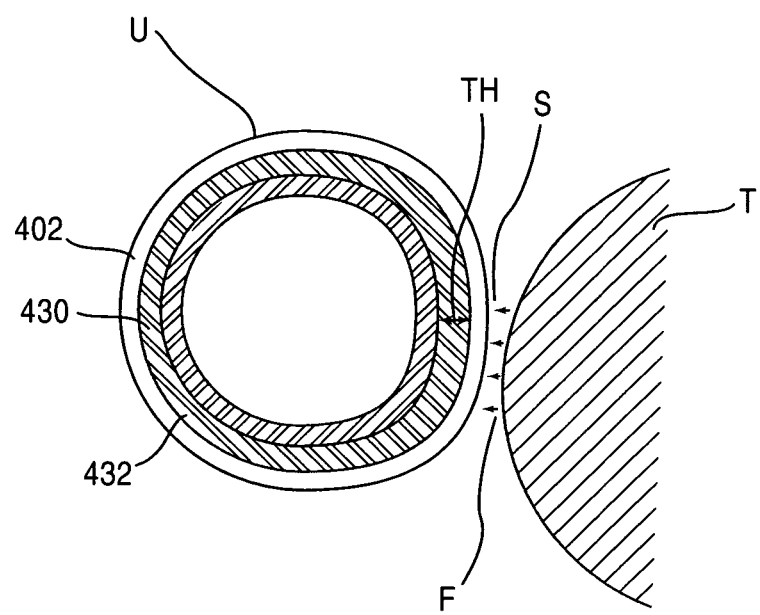
FIG. 6 is a cross-sectional view of a reinforcement member having a side wall having variable thickness according to an embodiment of the invention.

For example, FIG. 6 shows a cross-sectional view of an alternative embodiment of a reinforcement member 430 according to an embodiment of the invention, the reinforcement member 430 being coupled to an elongate member 402 that is disposed within the ureter U of a patient. In the illustrated embodiment, the thickness TH of the side wall 432 of the reinforcement member 430 varies circumferentially, thereby causing the strength of the reinforcement member 430 to vary circumferentially. As illustrated, the orientation of the reinforcement member 430 on the elongate member 402 can be varied circumferentially so that region having a thicker side wall 432 is adjacent to the stricture S. In this manner, the reinforcement member 430 can be oriented circumferentially to resist deformation caused by the external force F caused by the tumor T, while minimizing the wall thickness TH in areas where increased strength is not required.

Other embodiments of the invention contemplate a reinforcement member configured to provide other therapeutic benefits in addition to increasing the strength of the ureteral stent. For example, the reinforcement member can be used to deliver a therapeutic agent to a specific location within the patient. The therapeutic agent can be applied as a coating disposed on the reinforcement member, or can be interspersed within a reinforcement member designed to dissolve upon contact with a bodily fluid. A variety of reinforcement members can be designed with different therapeutic agents or dosage levels, thereby offering practitioners a flexible method of administering drugs.

In yet other embodiments of the invention, some or all of the reinforcement member contains a radiopaque material to allow the practitioner to visualize the position of the stent while it is within the patient using standard imaging techniques.

Figure 7A:
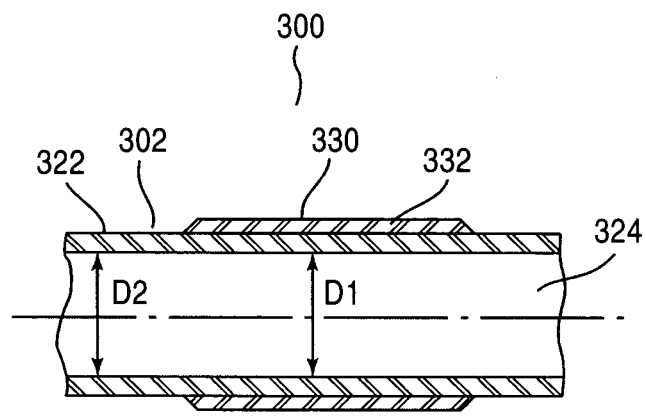
FIGS. 7A and 7B are cross-sectional views of ureteral stents according to two embodiments of the invention.

FIG. 7A shows a cross-sectional view of the elongate member 302 of the ureteral stent 300 in the region where the reinforcement member 330 is disposed. As described above, the elongate member 302 extends through the lumen defined by the reinforcement member 330 so that the reinforcement member 330 acts as a sleeve over the outer surface of the side wall 322 of the elongate member 302. The reinforcement member 330 is further configured such that it does not cause any reduction in the cross-sectional area defined by the lumen 324 of the elongate member 302. In other words, when the lumen 324 of the elongate member 302 has a circular cross-section, the diameter D1 of the elongate member 302 at a location where the reinforcement member 330 is disposed is substantially the same as the diameter D2 of the elongate member 302 at a location where the elongate member 330 is not disposed.

Figure 7B:
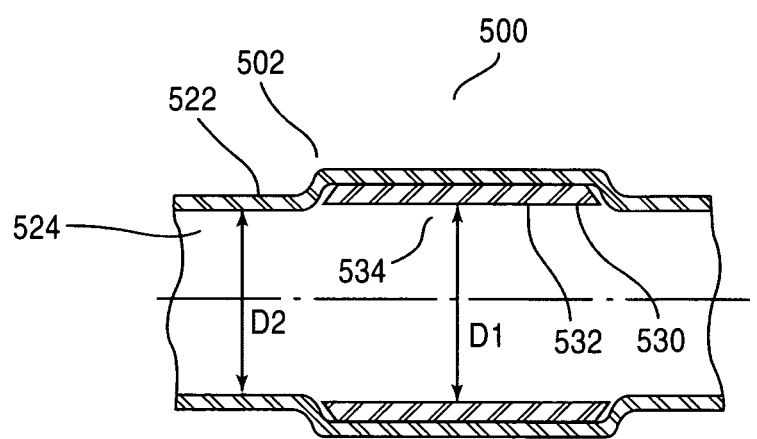

FIG. 7B illustrates a portion of a ureteral stent 500 according to another embodiment of the invention. The reinforcement member 530 of the ureteral stent 500 is disposed within the lumen 524 of the elongate member 502. The reinforcement member 530 is further configured such that when it is disposed within the elongate member 502, the cross-sectional area defined by the side wall 532 of the reinforcement member 530 is not less than the cross-sectional area defined by the side wall 522 of the elongate member 502. For example, where lumens 524 and 534 have circular cross-sections, the diameter D1 in the region where the reinforcement member 530 is located is at least as large as the diameter D2 in the region devoid of the reinforcement member 530. This may be accomplished by a reinforcement member 530 having sufficient strength to cause the side wall 522 of the elongate member 502 to expand when the reinforcement member 530 is inserted into the lumen 524 of the elongate member 502. Alternatively, the reinforcement member 530 can be configured to expand upon being positioned within the elongate member 502 thereby ensuring that its cross-sectional area is not reduced. Expansion of the reinforcement member 530 can also provide increased resistance to deformation when the stent is subjected to external forces from a stricture.

Although both FIGS. 7A and 7B describe the elongate member and reinforcement member as defining lumens having a circular cross-section, the present invention contemplates lumens having any cross-sectional shape. The present invention also contemplates a ureteral stent that does not include a side wall that defines a lumen. Furthermore, while the installation of the reinforcement member does not in itself create a reduction in the cross-sectional area of the lumen, it should be understood that the external forces created by the stricture or tumor can cause some reduction in the cross-sectional area of the ureteral stent.

Figure 8A:
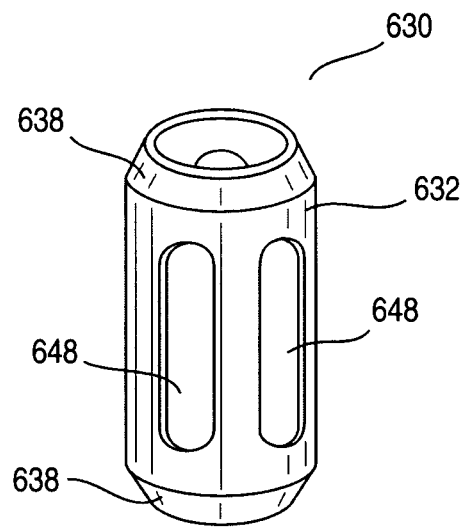
FIGS. 8A through 8E are perspective views of reinforcement members according to several embodiments of the invention.
Figure 8B:
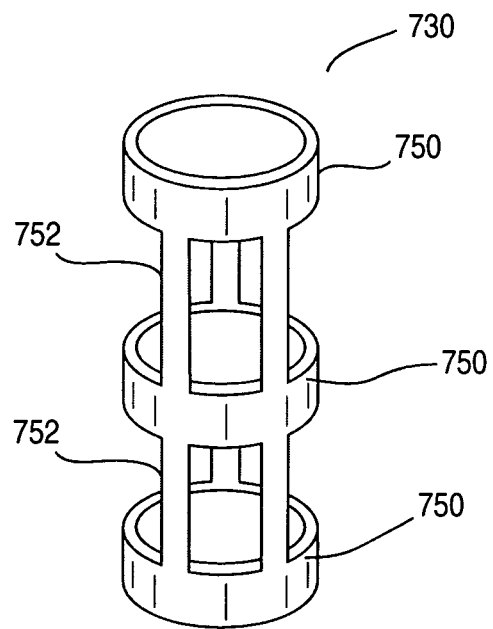

FIGS. 8A through 8E show various reinforcement members according to several embodiments of the invention. FIG. 8A shows a reinforcement member 630 having a side wall 632 that defines a series of slots 648. Reinforcement member 630 also includes tapered edges 638 to reduce patient discomfort during stent insertion. Similarly, FIG. 8B shows a reinforcement member 730 that is comprised of a series of structural rings 750 connected by axial connection members 752.

Figure 8C:
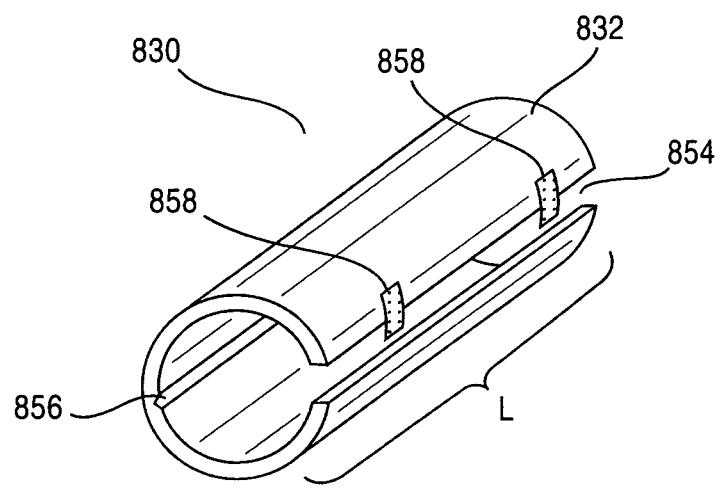
Figure 8D:
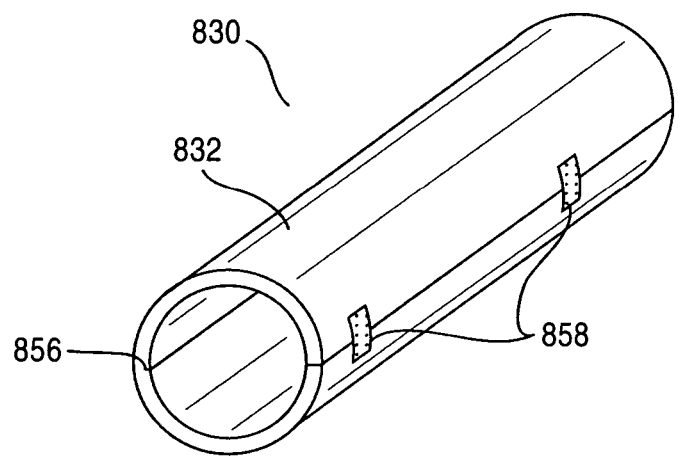
Figure 8E:
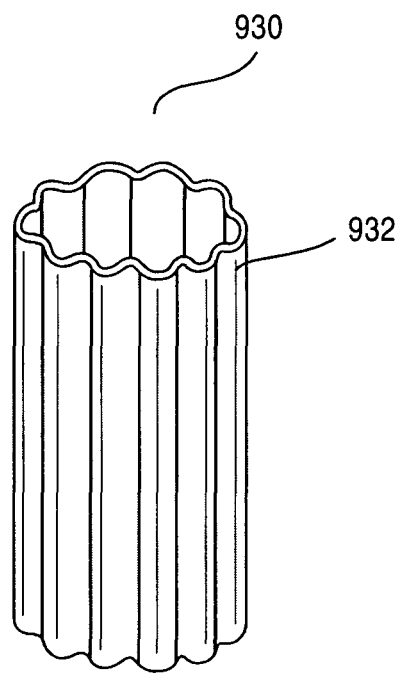

FIGS. 8C and 8D show an alternative embodiment of the reinforcement member 830 having a side wall 832 defining an opening 854 extending the entire length L of the reinforcement member 830. The "c-channel" design allows the practitioner to open the reinforcement member 830 thus allowing it to easily slip over the elongate member in the desired region. As illustrated, the reinforcement member 830 includes a notch 856 defining a living hinge to facilitate easy expansion of the reinforcement member 830. In other embodiments, the reinforcement member can include any type of hinge mechanism. In the illustrated embodiment, the reinforcement member has two clips 858 to secure the side wall 832 in a closed position when placed on the elongate member (not shown in FIG. 8D). Alternatively, the reinforcement member 830 can be secured in the closed position by any other suitable mechanism, such as an adhesive.

Alternative embodiments can include reinforcement members having side walls with cross-sectional shapes configured to increase the strength of the reinforcement member. For example, the reinforcement member 930 illustrated in FIG. 8E has a side wall 932 having a corrugated shape.

Figure 9A:
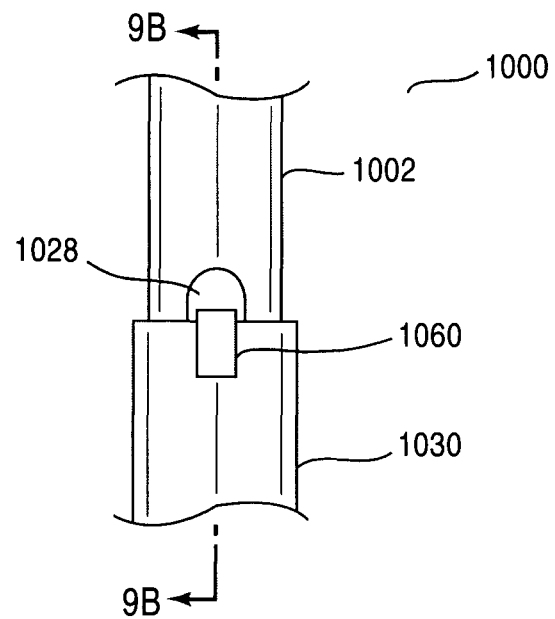
FIG. 9A is side view of a portion of a ureteral stent showing a reinforcement member attached to an elongate member by an attachment member according to an embodiment of the invention.
Figure 9B:
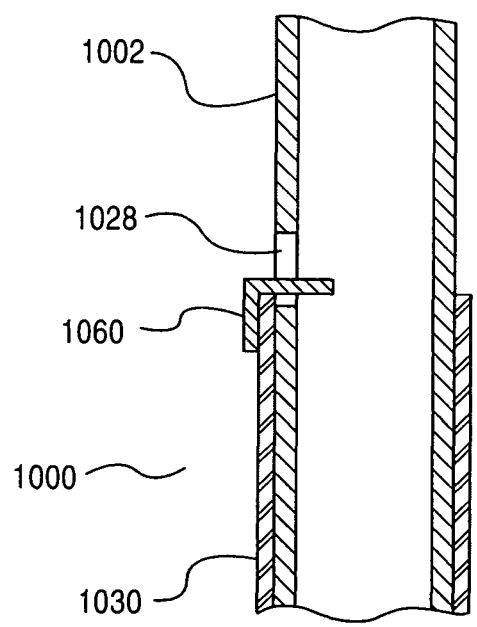
FIG. 9B is cross-sectional view of the ureteral stent of FIG. 9A taken along line 9B-9B in FIG. 9A.

FIGS. 9A and 9B show a ureteral stent 1000 according to another embodiment of the invention. The ureteral stent 1000 includes a reinforcement member 1030 that is attached to the elongate member 1002 by an attachment member 1060. As shown in illustrated embodiment, the attachment member 1060 is a clip that attaches to the elongate member 1002 via a side port 1028. Accordingly, the reinforcement member 1030 can be coupled to the elongate member 1002 at any of the side ports 1028 included in the elongate member 1002. In other embodiments, however, the attachment member can be any fastener, such as a suture or a band-type clamp suitably designed to secure the reinforcement member to the elongate member without constricting the lumen of the elongate member.

Figure 10A:
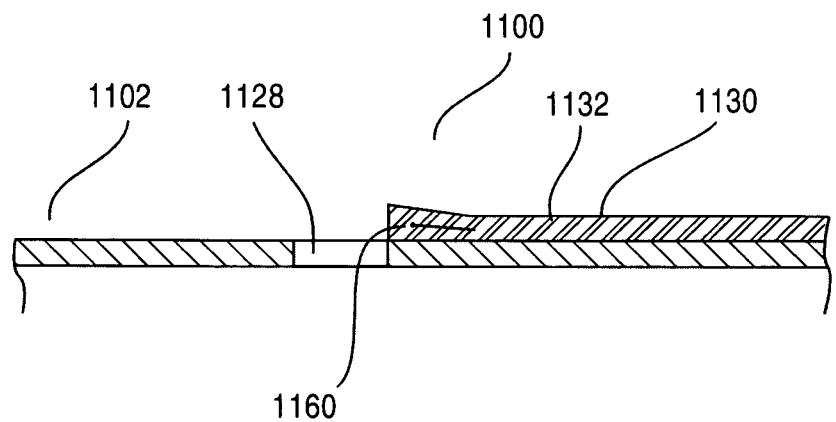
FIGS. 10A and 10B are cross-sectional views of a ureteral stent that includes a reinforcement member having an integral attachment member according to an embodiment of the invention.
Figure 10B:
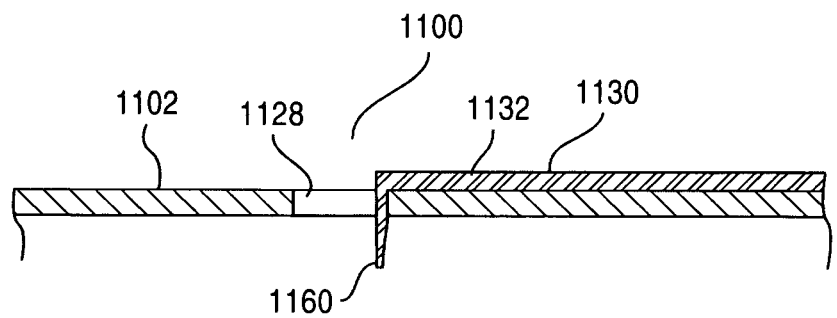
Figure 10C:
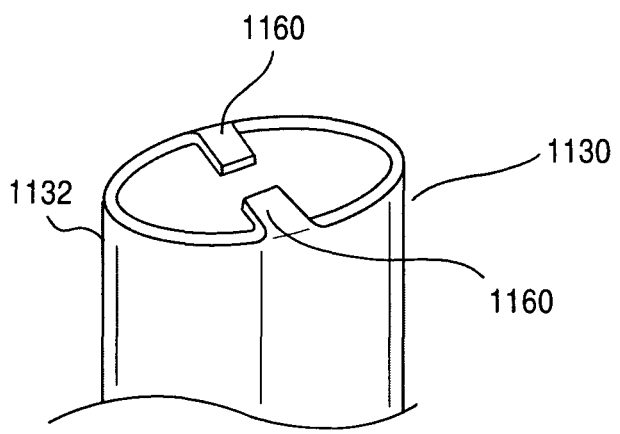
FIG. 10C is a perspective view of the reinforcement member of FIGS. 10A and 10B.

FIGS. 10A through 10C show a ureteral stent 1100 according to an embodiment of the invention whereby the reinforcement member 1130 contains an integral attachment member 1160. As illustrated, the attachment member 1160 is a clip designed to engage in one of the side ports 1128 when the reinforcement member 1130 is in its desired position. As shown in FIG. 10A, the integral attachment member 1160 is folded underneath the reinforcement member 1130 when the reinforcement member 1130 is placed on the elongate member 1102. When the reinforcement member 1130 reaches the desired position, the practitioner can then align the integral attachment member 1160 with one of the side ports 1128, allowing the integral attachment member 1160 to spring into place within the side port 1128, securing the reinforcement member into position, as shown in FIG. 10B. FIG. 10C shows the reinforcement member 1130 prior to being disposed on the elongate member 1102. In the illustrated embodiment, the reinforcement member 1130 includes two integral attachment members 1160. Alternatively, in other embodiments, the reinforcement member can include any number of integral attachment members.

Although the above embodiments are illustrated and described as employing a mechanical fastener to secure the reinforcement member in position, it is not necessary that a mechanical fastener be used. For example, the reinforcement member can be secured into place by an adhesive or other chemical bond. Alternatively, the reinforcement member can be secured in place by frictional forces produced by the elastic properties of the reinforcement member itself, as in the case where the reinforcement member is designed to expand against the elongate member. Finally, the reinforcement member can be allowed to "float" while the ureteral stent is being inserted into the patient. In such instances, the external forces imposed by the stricture or tumor may be sufficient to secure the reinforcement member in the desired position.

While the ureteral stents are shown and described above as including one reinforcement member, in some embodiments, a ureteral stent can include multiple reinforcement members.

Figure 11:
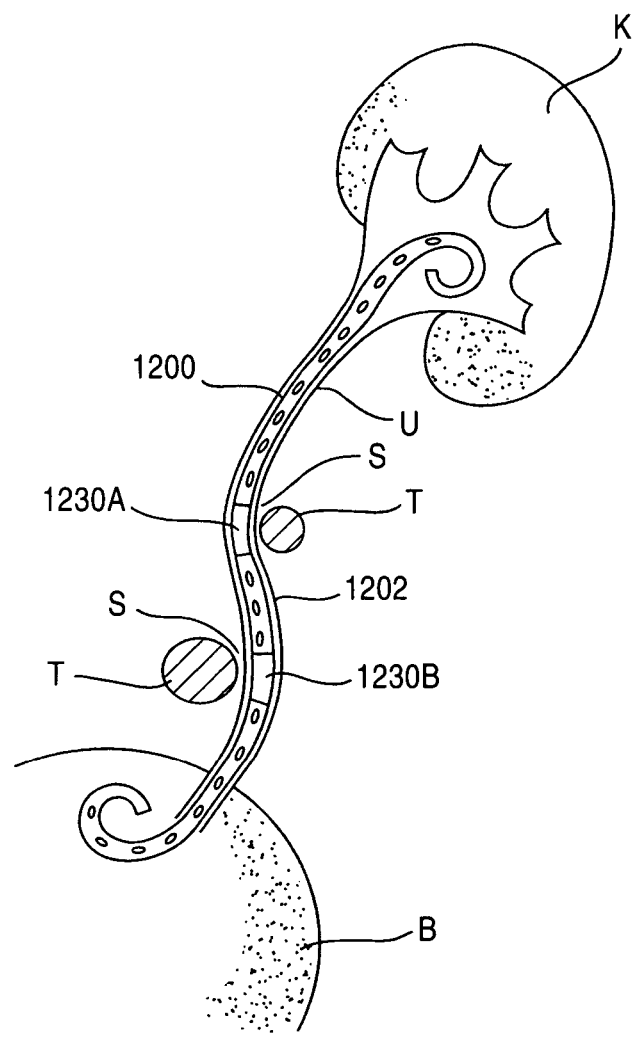
FIG. 11 illustrates a ureteral stent disposed within the urinary tract of a patient, the ureteral stent including two reinforcement members according to an embodiment of the invention.

For example, FIG. 11 shows a ureteral stent 1200 that includes two reinforcement members 1230A and 1230B according to an embodiment of the invention. The ureteral stent 1200 is positioned within a patient such that it extends from a kidney K, through a ureter U, and to a bladder B. As illustrated, the ureter U is affected by a two strictures S, each caused by a tumor T. The reinforcement members 1230A and 1230B are therefore coupled to the elongate member 1202 of the ureteral stent 1200 at locations adjacent to the strictures S to provide resistance to deformation as described above.

Although FIG. 11 shows a ureteral stent 1200 having two reinforcement members 1230A and 1230B, in some embodiments a ureteral stent can have any number of reinforcement members. Such reinforcement members can be positioned at any number of axial positions along the elongate member and/or any number of circumferential orientations on the elongate member as circumstances require. Although the ureteral stent 1200 illustrated in FIG. 11 shows that the two reinforcement members 1230A and 1230B are spaced apart axially, in some embodiments, the reinforcement members can directly abut or overlap each other. Furthermore, the multiple reinforcement members can have different lengths, be made of different materials, and/or have different physical properties, as the circumstances require.

CONCLUSION

While various embodiments of the invention have been described above, it should be understood that they have been presented by way of example only, and not limitation. For example, while the invention is shown and described as including a ureteral stent, in other embodiments the invention may include any medical device configured to convey a fluid within the body of a patient, such as, for example, a ureteral catheter.

What is claimed is:

1. A medical device comprising:
    a stent having a side wall defining a lumen configured to convey a fluid within a body of a patient, the stent having a proximal retention portion configured to retain at least a portion of the stent in a bladder of the patient and a distal retention portion configured to retain at least a portion of the stent in a kidney of the patient, at least one of the proximal retention portion and the distal retention portion including a hook or a loop; and
    a reinforcement member including a side wall defining a lumen, the stent configured to be received within the lumen of the reinforcement member such that the reinforcement member can be slidably moved to a first axial location along an outer surface of the stent and removably coupled thereto such that the reinforcement member can be uncoupled and slidably moved to a second axial location along an outer surface of the stent, the reinforcement member having a clip including a protrusion, the protrusion being configured for insertion in a side port of the side wall of the stent when the stent is received within the lumen of the reinforcement member.

2. The medical device of claim 1, wherein the stent is configured to extend through the lumen defined by the side wall of the reinforcement member such that the side wall of the stent and the side wall of the reinforcement member are substantially concentric.

3. The medical device of claim 1, wherein the stent has a length that is greater than a length of the reinforcement member.

4. The medical device of claim 1, wherein the stent includes a proximal portion including the proximal retention portion, a distal portion including the distal retention portion, and a medial portion disposed between the proximal portion and the distal portion, the reinforcement member being configured to be coupled to the medial portion.

5. The medical device of claim 1, wherein when the reinforcement member is coupled to the side wall of the stent at the first axial location, the stent has a degree of resistance to deformation at the first axial location that is greater than a degree of resistance to deformation of a portion of the stent devoid of the reinforcement member.

6. The medical device of claim 1, wherein when the reinforcement member is coupled to the side wall of the stent at the first axial location and the side wall of the stent is subjected to pressure from a stricture where the reinforcement is coupled, the lumen defined by the side wall of the stent at the first axial location has a cross-sectional area at least as large as a cross-sectional area of the lumen defined by the side wall at a portion of the stent that is not within the lumen of the reinforcement member.

7. The medical device of claim 1, wherein the reinforcement member includes a therapeutic agent.

8. The medical device of claim 1, wherein the reinforcement member includes an adhesive configured to couple the reinforcement member to the stent.

9. The medical device of claim 1, wherein the reinforcement member includes a radiopaque material.

10. The medical device of claim 1, wherein the reinforcement member is configured to be coupleable to the side wall of the stent in either of a first circumferential orientation on the stent and a second circumferential orientation on the stent, the second circumferential orientation being circumferentially offset from the first circumferential orientation.

11. The medical device of claim 1, wherein the reinforcement member is one of a plurality of reinforcement members, each of the plurality of reinforcement members configured to be coupleable to the side wall of the stent at any of the first axial location, the second axial location, and a third axial location of the stent, the third axial location being axially offset from the first axial location and the second axial location.

12. The medical device of claim 1, wherein a side wall of the reinforcement member has a thickness that varies circumferentially.

13. The medical device of claim 1, wherein the stent retains its shape when the reinforcement member is coupled to the stent.

14. The medical device of claim 1, wherein the reinforcement member is configured to be removably coupled to the outer surface of the stent such that an entire length of the reinforcement member is disposed on the outer surface of the stent.

15. The medical device of claim 1, wherein the proximal retention portion includes a "J" hook.

16. The medical device of claim 1, wherein the proximal retention portion includes a curved loop.

17. A method of selectively reinforcing a portion of a ureteral stent comprising:
    selecting a portion of the stent to be reinforced such that the portion will be disposed proximate to a stricture in a ureter of a patient when the ureteral stent is inserted into the ureter;
    sliding a reinforcement member having a clip including a protrusion along an outer surface of the stent to the selected portion of the stent;
    coupling the reinforcement member to the selected portion of the stent such that the reinforcement member may be removed from the selected portion of the stent and moved to a different portion of the stent, the coupling including inserting the protrusion of the clip in a side port of the outer surface of the stent, and inserting the ureteral stent into a body of the patient such that a proximal retention portion of the ureteral stent is disposed within a bladder of the patient and a distal retention portion of the ureteral stent is disposed within a kidney of the patient, at least one of the proximal retention portion and the distal retention portion including a hook or a loop.

18. The method of claim 17, wherein the inserting the ureteral stent includes inserting the ureteral stent into the ureter of the patient such that the reinforcement member is disposed proximate to the stricture.

* * * * *